US005689009A

United States Patent [19]
Lefranc

[11] Patent Number: 5,689,009
[45] Date of Patent: Nov. 18, 1997

[54] PREPARATION OF HYDROXYBENZALDEHYDES

[75] Inventor: Helene Lefranc, Chaponost, France

[73] Assignee: Rhone-Poulenc Chimie, Courbevoie Cedex, France

[21] Appl. No.: 387,088

[22] Filed: Feb. 13, 1995

[30] Foreign Application Priority Data

Feb. 11, 1994 [FR] France .................. 94 01562

[51] Int. Cl.$^6$ ............................ C07C 45/38
[52] U.S. Cl. ............................ 568/432
[58] Field of Search ..................... 568/432

[56] References Cited

U.S. PATENT DOCUMENTS

| | | | |
|---|---|---|---|
| 3,290,393 | 12/1966 | Marchand et al. | 260/621 |
| 3,321,526 | 5/1967 | Marchand et al. | 260/600 |
| 4,026,950 | 5/1977 | LeLudec | 260/600 R |
| 4,306,083 | 12/1981 | Ma | 568/432 |
| 4,351,962 | 9/1982 | Gradeff et al. | 568/432 |
| 4,366,325 | 12/1982 | Wedemeyer et al. | 568/432 |

OTHER PUBLICATIONS

Chemical Abstracts, vol. 86, No. 11, Mar. 14, 1977, Columbus, Ohio; abstract No. 7212p, Cerveny, Libor et al, p. 568, col. 1; & Chem. Tech., vol. 28, p. 9, 1976.

*Primary Examiner*—C. Warren Ivy
*Assistant Examiner*—Jean F. Vollano
*Attorney, Agent, or Firm*—Burns, Doane, Swecker & Mathis, L.L.P.

[57] ABSTRACT

Hydroxybenzaldehydes, for example salicylaldehyde, are prepared in high yields by oxidizing the corresponding hydroxybenzyl alcohols, e.g., saligenol, with molecular oxygen or an oxygen-containing gas, in liquid phase, in an aqueous reaction medium containing an alkali, in the presence of (i) a catalytically effective amount of a platinum catalyst and (ii) a cocatalytically effective amount of boron and bismuth compounds.

29 Claims, No Drawings

PREPARATION OF HYDROXYBENZALDEHYDES

BACKGROUND OF THE INVENTION

1. Field of the Invention

The present invention relates to the oxidation of hydroxybenzyl alcohols into their corresponding hydroxybenzaldehydes, and, more especially, to the preparation of salicylic aldehyde from ortho-hydroxybenzyl alcohol (i.e., saligenol, or salicyl alcohol).

2. Description of the Prior Art

A number of techniques are known to this art for carrying out the oxidation process indicated above.

In particular, FR-A-2,305,420 describes the oxidation of ortho-hydroxybenzyl alcohol in the liquid phase, using molecular oxygen or a gas containing molecular oxygen, in an aqueous medium containing an alkali, in the presence of a platinum- or palladium-based catalyst. The reaction is characterized in that the oxidation is carried out in the presence of a cocatalyst based on a bismuth compound.

The yields employing platinum-based compounds, which provide better reaction yields than palladium-based catalysts, are increased in accordance with this particular prior art process due to the presence of the bismuth. Thus, the published salicylic aldehyde yields are 77.6% in the absence of bismuth, and 92.8% in the presence of bismuth.

SUMMARY OF THE INVENTION

Accordingly, a major object of the present invention is the provision of an improved process for the preparation of a hydroxybenzaldehyde by oxidation of the corresponding hydroxybenzyl alcohol in the liquid phase, by means of molecular oxygen or a gas containing molecular oxygen, in an aqueous reaction medium containing an alkali and in the presence of a platinum-based catalyst, and further wherein such oxidation is carried out in the presence of cocatalytically effective amounts of a boron compound and a bismuth compound.

DETAILED DESCRIPTION OF BEST MODE AND PREFERRED EMBODIMENTS OF THE INVENTION

More particularly according to the present invention, it has now unexpectedly and surprisingly been determined that the presence of the boron compound cocatalyst, together with the bismuth compound cocatalyst, permits even higher yields of salicylaldehyde to be attained, i.e., on the order of up to 97%, upon the $O_2$ oxidation of saligenol.

The presence of the boron limits the oxidation to the aldehyde stage, without forming the acid.

The process of the invention is applicable to any hydroxybenzyl alcohol, i.e., to any aromatic compound having at least one —OH group and one —CH$_2$OH group.

By the term "aromatic compound" is intended the conventional concept of aromaticity as defined in the literature, in particular by Jerry March, *Advanced Organic Chemistry*, 3rd edition, John Wiley & Sons, p. 37 ff (1985).

The process of this invention is particularly suitable for the oxidation of hydroxybenzyl alcohols having the following formula (I):

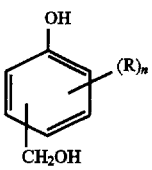

in which the radical —CH$_2$OH is in the ortho-, meta- or para-position with respect to the hydroxy group, the benzene nucleus may be substituted by one or more inert substituents R, which may be identical or different, and n is a number which is less than or equal to 3.

In the following description of the present invention, the radical of the formula:

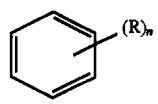

is represented by the symbol "Ar".

Any substituent can be present on the benzene nucleus provided that it does not interfere with the desired final product. Exemplary substituents R include, in particular, halogen atoms, preferably fluorine, chlorine or bromine, and alkyl or alkoxy radicals, preferably having from 1 to 12 carbon atoms, more preferably from 1 to 4 carbon atoms.

Exemplary preferred hydroxybenzyl alcohols include:

2-Hydroxybenzyl alcohol;

2-Hydroxy-4-methylbenzyl alcohol;

2-Hydroxy-6-methylbenzyl alcohol;

2-Hydroxy-6-ethoxybenzyl alcohol;

2-Hydroxy-6-chlorobenzyl alcohol.

The process of the invention is particularly applicable for the industrial scale preparation of salicylic aldehyde by oxidation of saligenol.

The boron compounds are preferably selected from among boric acids such as orthoboric acid, typically designated boric acid (or its precursor $B_2O_3$), metaboric acid, pyroboric acid and tetraboric acid.

Metallic borates can also be used, in particular those of alkali or alkaline earth metals, or of ammonium, in their anhydrous or hydrated states, in particular tertiary borates, hemiborates, monoborates, diborates, triborates, tetraborates or pentaborates, preferably of alkali metals, or of ammonium.

A double salt containing boron can also be used, in particular metallic fluoborates, for example potassium fluoborate.

Suitable such boron compounds include:

Sodium orthoborate;

Potassium orthoborate;

Sodium monohydrogen orthoborate;

Potassium monohydrogen orthoborate;

Sodium dihydrogen orthoborate;

Potassium dihydrogen orthoborate;

Orthoboric acid or its precursor, boric anhydride;

Sodium metaborate;

Tetrahydrated sodium metaborate;

Sodium tetraborate;

Decahydrated sodium tetraborate, or borax;

Pentahydrated sodium tetraborate;

Potassium metaborate;

Tetrahydrated potassium pentaborate;
Octahydrated potassium tetraborate;
Tetrahydrated ammonium pentaborate;
Tetrahydrated ammonium tetraborate.

Boric acid or boric anhydride is the preferred.

The amount of boron compound employed is determined such that the ratio between the number of moles of boron compound and the number of moles of hydroxybenzyl alcohol ranges from 0.1 to 3.0, preferably from 0.9 to 1.1.

The cocatalyst is typically an inorganic or organic bismuth compound in which the bismuth atom has an oxidation state greater than zero, for example 2, 3, 4 or 5. The residue associated with the bismuth atom is not critical as long as this condition is satisfied. The cocatalyst can be either soluble or insoluble in the medium of reaction.

Exemplary cocatalysts suitable for use in the process of the present invention include the bismuth oxides; bismuth hydroxides; salts of mineral hydrogen acids such as bismuth chloride, bromide, iodide, sulfide, selenide or telluride; salts of mineral oxyacids such as bismuth sulfite, sulfate, nitrite, nitrate, phosphite, phosphate, pyrophosphate, carbonate, perchlorate, antimonate, arsenate, selenite or selenate; salts of oxyacids derived from transition metals, such as bismuth vanadate, niobate, tantalate, chromate, molybdate, tungstate or permanganate.

Other suitable compounds include salts of organic aliphatic or aromatic acids, such as bismuth acetate, propionate, benzoate, salicylate, oxalate, tartrate, lactate or citrate; and phenates, such as bismuth gallate or pyrogallate. These salts and phenates may also be bismuthyl salts.

Other inorganic or organic compounds that can thus be employed are binary compounds of bismuth with elements such as phosphorus and arsenic; heteropolyacids containing bismuth and their salts; also aliphatic or aromatic bismuthines.

Specific examples include:

(i) oxides: BiO; $Bi_2O_3$; $Bi_2O_4$; $Bi_2O_5$;

(ii) hydroxides: $Bi(OH)_3$;

(iii) salts of mineral hydrogen acids: bismuth chloride $BiCl_3$, bismuth bromide $BiBr_3$, bismuth iodide $BiI_3$, bismuth sulfide $Bi_2S_3$, bismuth selenide $Bi_2Se_3$, bismuth telluride $Bi_2Te_3$;

(iv) salts of mineral oxyacids: basic bismuth sulfite $Bi_2(SO_3)_3$, $Bi_2O_3 \cdot 5H_2O$, neutral bismuth sulfate $Bi_2(SO_4)_3$, bismuthyl sulfate $(BiO)HSO_4$, bismuthyl nitrite $(BiO)NO_2 \cdot 0.5H_2O$, neutral bismuth nitrate $Bi(NO_3)_3 \cdot 5H_2O$, the double nitrate of bismuth and magnesium $2Bi(NO_3)_3, 3Mg(NO_3)_2 \cdot 24H_2O$, bismuthyl nitrate $(BiO)NO_3$, bismuth phosphite $Bi_2(PO_3H)_3 \cdot 3H_2O$, neutral bismuth phosphate $BiPO_4$, bismuth pyrophosphate $(Bi_4(P_2O_7)_3$, bismuthyl carbonate $(BiO)_2CO_3 \cdot 0.5H_2O$, neutral bismuth perchlorate $Bi(ClO_4)_3 \cdot 5H_2O$, bismuthyl perchlorate $(BiO)ClO_4$, bismuth antimonate $BiSbO_4$, neutral bismuth arsenate $Bi(AsO_4)_3$, bismuthyl arsenate $(BiO)AsO_4 \cdot 5H_2O$, bismuth selenite $Bi_2(SeO_3)_3$;

(v) salts of oxyacids derived from transition metals: bismuth vanadate $BiVO_4$, bismuth niobate $BiNbO$, bismuth tantalate $BiTaO_4$, neutral bismuth chromate $Bi_2(CrO_4)$, bismuthyl dichromate $(BiO)_2Cr_2O_7$, acidic bismuthyl chromate $H(BiO)CrO_4$, the double chromate of bismuthyl and potassium $K(BiO)CrO_{10}$, bismuth molybdate $Bi_2(MoO_4)_3$, bismuth tungstate $Bi_2(WO_4)_3$, the double molybdate of bismuth and sodium $NaBi(MoO_4)_2$, basic bismuth permanganate $Bi_2O_2(OH)MnO_4$;

(vi) salts of organic aliphatic or aromatic acids: bismuth acetate $Bi(C_2H_3O_2)_3$, bismuthyl propionate $(BiO)C_3H_5O_2$, basic bismuth benzoate $C_6H_5CO_2Bi(OH)_2$, bismuthyl salicylate $C_6H_4CO_2(BiO)(OH)$, bismuth oxalate $(C_2O_4)_3Bi_2$, bismuth tartrate $Bi_2(C_4H_4O_6)_3 \cdot 6H_2O$, bismuth lactate $(C_6H_5O_5)OBi \cdot 7H_2O$, bismuth citrate $C_6H_5O_7Bi$;

(vii) phenates: basic bismuth gallate $C_7H_7O_7Bi$, basic bismuth pyrogallate $C_6H_3(OH)_2(OBi)(OH)$.

Other suitable inorganic or organic compounds include bismuth phosphide BiP, bismuth arsenide $Bi_3As_4$, sodium bismuthate $NaBiO_3$, bismuth/thiocyanic acids $H_2[Bi(BNS)_5]$, $H_3[Bi(CNS)_6]$ and their sodium and potassium salts, trimethylbismuthine $Bi(CH_3)_3$, and triphenylbismuthine $Bi(C_6H_5)_3$.

The preferred bismuth compounds according to the process of the invention are bismuth oxides, bismuth hydroxides, the bismuth or bismuthyl salts of mineral hydrogen acids, the bismuth or bismuthyl salts of mineral oxyacids, the bismuth or bismuthyl salts of organic aliphatic or aromatic acids, and bismuth or bismuthyl phenates.

Particularly preferred bismuth compound cocatalysts according to this invention are bismuth oxides $Bi_2O_3$ and $Bi_2O_4$, bismuth hydroxide $Bi(OH)_3$, neutral bismuth sulfate $Bi_2(SO_4)_3$, bismuth chloride $BiCl_3$, bismuth bromide $BiBr_3$, bismuth iodide $BiI_3$, neutral bismuth nitrate $Bi(NO_3)_3 \cdot 5H_2O$, bismuthyl nitrate $BiO(NO_3)$, bismuthyl carbonate $(BiO)_2CO_3 \cdot 0.5H_2O$, bismuth acetate $Bi(C_2H_3O_2)_3$, bismuthyl salicylate $C_6H_4CO_2(BiO)(OH)$.

The amount of cocatalyst used, expressed as the amount of metallic bismuth contained in the cocatalyst with respect to the weight of platinum employed, can vary over wide limits. This amount can be as low as 0.1%, for example, and can also equal or exceed the amount of platinum employed without detriment.

More particularly, the amount is selected such that the concentration of metallic bismuth with respect to the hydroxybenzyl alcohol in the oxidation medium ranges from 10 to 900 ppm by weight. The cocatalyst can be used in amounts in excess of about 900 to 1,500 ppm, but there is no great additional advantage presented thereby.

The platinum used conjointly as the reaction catalyst can be in a variety of forms, for example platinum black, platinum oxide, or the noble metal itself deposited onto a variety of supports such as carbon black, calcium carbonate, activated aluminas and silicas, or equivalent materials. Catalytic substrates based on carbon black are particularly suitable.

The amount of catalyst used, expressed as the weight of metallic platinum with respect to that of the alcohol to be oxidized, can range from 0.01% to 4%, preferably from 0.04% to 2%.

The concentration of alcohol to be oxidized in the aqueous alkali solution is preferably such that precipitation is avoided and a homogeneous solution is maintained.

The concentration of alcohol in the aqueous solution generally ranges from 1% to 60% by weight, preferably from 2% to 30% by weight.

In accordance with the process of the invention, the oxidation is carried out in an aqueous medium containing an alkali in solution. The alkali is typically sodium or potassium hydroxide. The proportion of inorganic base used ranges from 0.5 to 3 moles of inorganic base per mole of alcohol to be oxidized.

One technique for carrying out the process entails contacting the aqueous solution containing the alcohol to be oxidized with the molecular oxygen or gas containing molecular oxygen, the alkali, the platinum based catalyst, the cocatalyst based on a bismuth compound and the boron compound, in the proportions indicated above. The operation is carried out at atmospheric pressure, but can if necessary be carried out under pressure. The mixture is then stirred at the desired temperature until the necessary amount of oxygen required to transform the alcohol into the aldehyde has been consumed. The progress of the reaction is thus monitored by measuring the amount of oxygen absorbed.

The reaction temperature depends on the thermal stability of the products formed.

In general, the reaction is carried out in the temperature range of 10° C. to 100° C., preferably 20° C. to 60° C.

Following cooling, if required, the catalytic mass is separated from the reaction mixture, for example by filtration, and the resulting liquid is acidified by addition of a protonic mineral acid, preferably sulfuric acid, to a pH of less than or equal to 6. The desired hydroxybenzaldehyde can then be isolated, for example by extraction using a suitable solvent (for example toluene) or by steam distillation, followed by purification utilizing known procedures.

In the process of the invention, in the event that hydroxybenzyl alcohol, more particularly saligenol, is prepared using the conventional techniques described in the literature, for example by condensation of phenol with formaldehyde in the presence of zinc acetate or calcium formate (GB-A-0,774,696), the boron compound can be introduced during oxidation.

In another embodiment of the invention, the boron compound is introduced during preparation of the starting hydroxybenzyl alcohol which is carried out via a specific reaction sequence, as particularly described in FR-A-1,328,945 and FR-A-2,430,928.

Thus, in a first step, a boric ester of phenol is prepared by reacting a phenol with boric acid (or boric anhydride), and then the boric ester of the phenol obtained is reacted with formaldehyde or a formaldehyde generator, for example trioxane.

The boric esters produced, simply designated "aryl borates," are complex mixtures of:

(a) phenol metaborates having the formula (II):

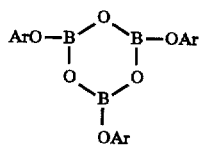

(b) phenol pyroborates having the formula (III):

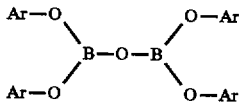

(c) phenol orthoborates having the formula (IV):

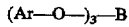 (IV)

(d) acid borates of phenols having the formula (V):

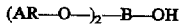 (V)

in which Ar is as defined above.

These mixtures may contain excess starting phenol.

The proportion of each of these boric acid derivatives in the esterification mixture depends on the molar ratio of phenol/boric acid employed. This ratio typically ranges from 0.8 to 3.0, preferably from 1.0 to 1.5.

Thus, for a phenol/boric acid ratio ranging from 1.0 to 1.5, the mixture is principally constituted by the metaborates of formula (II); for ratios ranging from 1.5 to 3.0, the mixture is principally constituted by phenol pyroborates of formula (III) and acid borates of formula (V). For a ratio of 3.0 or close to 3.0, orthoborates of formula (IV) are essentially the only components of the mixture.

Aryl borates are prepared using known procedures, by reacting a phenol with boric acid.

The phenol preferably has the formula:

 (VI)

in which Ar is as defined above.

Exemplary phenols of formula (VI) include phenol, cresols, 2,3-xylenol, 2,4-xylenol, 2,5-xylenol, 3,4-xylenol, monomethylphenols, monoethylphenols, monopropylphenols, monobutylphenols, monomethyl-, monoethyl-, monopropyl- and monobutylethers of pyrocatechol, hydroquinone or resorcinol, monochlorophenols, 2,3-dichlorophenol, 2,4-dichlorophenol, 2,5-dichlorophenol, 3,4-dichlorophenol, 3,5-dichlorophenol, 2,4,5-trichlorophenol, 2,3,5-trichlorophenol, 2,3-dimethoxyphenol and 3,5-dimethoxyphenol.

The preparation of an aryl borate by reacting a phenol with boric acid is carried out in a solvent medium which forms an azeotrope with the water emanating from the esterification reaction. This latter is eliminated as it is formed by azeotropic distillation. Suitable solvents for the preparation of aryl borates are aromatic hydrocarbons such as benzene, toluene or xylene. Any other inert solvent permitting azeotropic distillation of water may be used.

The condensation is carried out in an anhydrous reaction medium. The solvent used for preparing the aryl borate can be used. Under these conditions, the borate is not isolated from the medium after esterification, but is directly reacted with the formaldehyde.

The formaldehyde is preferably employed in an amount of 1 mole per mole of boric acid. It can deviate from this value without detriment and may range from 0.9 to 1.1.

When a formaldehyde generator is used, the amount of formaldehyde is calculated such that the amount of formaldehyde available for reaction falls within the range defined above.

The temperature at which the formaldehyde or its generator is condensed with the selected phenol ranges from 20° C. to 120° C., preferably from 40° C. to 100° C.

A hydroxybenzyl alcohol borate is thus produced.

In a subsequent step, the hydroxybenzyl alcohol is liberated from the condensation medium via any known technique, for example by saponification, hydrolysis or alcoholysis.

Saponification is the preferred procedure, entailing treating the reaction medium with a base. The base is preferably an alkali metal hydroxide, more preferably sodium or potassium hydroxide.

The amount of base introduced depends on the nature of the aryl borate and ranges from 2.0 to 4.0 moles, preferably about 2.0 moles of alkaline base per mole of boric acid employed.

Following saponification, the complex alkaline salt of hydroxybenzyl alcohol and boric acid is in an aqueous solution which can be directly used for an oxidation reaction carried out in the presence of platinum and bismuth, without the requirement for separating the constituents thereof.

Salicylic aldehyde can thus be prepared directly from phenol without isolating the intermediate products formed.

Thus, the phenol is reacted with boric acid (or boric anhydride) to form a boric ester, which latter is then reacted with formaldehyde to produce a saligenine borate which, after saponification using an alkaline base, provides an aqueous solution of a complex alkaline salt of saligenol and boric acid. This aqueous solution can then be used directly for oxidation in the presence of a platinum based catalyst and a co-catalyst based on a bismuth compound without having to separate the constituents thereof.

Very high yields of salicylic aldehyde are obtained after oxidation employing the process of the invention.

The process of the invention is of particular interest for the preparation of salicylic aldehyde which can be used, inter alia, for the synthesis of cumarin (or coumarin).

Salicylic aldehyde prepared via the process of the invention can be used as a starting material for the synthesis of cumarin: this is prepared by a known cyclization step which has been widely described in the literature. In particular, the Perkin reaction for the preparation of cumarin is representative thereof, by reacting salicylic anhydride with acetic anhydride in the presence of sodium acetate (KIRK-OTHMER, *Encyclopedia of Chemical Technology*, 7, p. 198, 3rd edition).

In order to further illustrate the present invention and the advantages thereof, the following specific examples are given, it being understood that same are intended only as illustrative and in nowise limitative.

In said examples to follow, the abbreviation Y (yield) has the definition:

$$Y = \frac{\text{number of moles of aldehyde formed}}{\text{number of moles of saligenol introduced}}$$

EXAMPLES 1 TO 4

The noble metal-based catalyst used in these four examples was platinum in the form of a catalyst containing 2% by weight of metal deposited onto carbon black. The amount employed, expressed as the weight of platinum with respect to that of the alcohol to be oxidized, was 0.036%.

The reactions reported in the examples were carried out in the presence or in the absence of boric acid.

When using boric acid, the amount used, expressed as the weight of boric acid with respect to that of the alcohol to be oxidized, was 51%.

The reactions in the examples were carried out in the presence or in the absence of a bismuth-based cocatalyst, in this instance bismuth oxide. The amount used, expressed as the weight of bismuth with respect to that of the alcohol to be oxidized, was 0.065%.

The procedure followed in each example was as follows:

A 100 cm$^3$ glass flask was provided with a central stirring system, a heating means, and a thermometer. It was connected to a pure oxygen supply to permit the volume of gas absorbed to be measured over time.

The following were introduced/charged into the reactor:

EXAMPLE 1

(i) 8 cm$^3$ of an aqueous 4N caustic soda solution (0.032 mole of caustic soda);

(ii) 72 mg of platinum-based catalyst (i.e., 1.44 mg of platinum);

(iii) 4 g (0.0323 mole) of ortho-hydroxybenzyl alcohol and 34 cm$^3$ of water.

EXAMPLE 2

The procedure of Example 1 was repeated, but 2.9 mg of bismuth oxide (2.6 mg of bismuth) were also introduced.

EXAMPLE 3

The procedure of Example 1 was repeated, but 8 cm$^3$ of an aqueous 4N (0.032 mole) caustic soda solution were added and the amount of diluting water was reduced by 8 cm$^3$ to retain the same alcohol concentration in the mixture to be oxidized.

EXAMPLE 4

The procedure of Example 3 was repeated, but 2.9 mg of bismuth oxide (2.6 mg of bismuth) were also introduced.

After charging the reactants (Examples 1 to 4), the reactor was purged with oxygen and connected to the oxygen supply under a slight pressure corresponding to the weight of a 30 cm column of water.

The reaction mixture was heated to a temperature of 45° C. and stirring was commenced (1,000 rpm).

The mixture was stirred at the above temperature and the mixture was stirred at 45° C. until oxidation was complete (no more oxygen absorbed).

The results of the reaction, i.e., the yields of salicylic aldehyde with respect to the alcohol to be oxidized, were determined by liquid chromatography, following acidification of the reaction mixture.

The results obtained are reported in the Table below:

TABLE

| Example | 1* | 2* | 3* | 4 |
|---|---|---|---|---|
| Boric acid/alcohol, by weight | 0 | 0 | 0.5 | 0.5 |
| % Pt/alcohol, 0.036 by weight | 0.036 | 0.036 | 0.036 | 0.036 |
| Weight of Bi$_2$O$_3$ | 0 | 2.9 mg | 0 | 2.9 mg |
| Bismuth/platinum, by weight | 0 | 1.8 | 0 | 1.8 |
| Bismuth/alcohol, ppm by weight | 0 | 650 | 0 | 650 |
| Caustic soda/alcohol, mole | 1 | 1 | 2 | 2 |
| Time | 1 h, 30 min | 45 mn | 8 h | 30 mn |
| Yield of aldehyde/alcohol used (Y) | 77.6% | 92.2% | 52% | 97% |

*Comparative example

EXAMPLE 5

The following reagents were charged into a 250 ml three-necked flask provided with a stirring apparatus, a heating sleeve and a column provided with a retrograder to reflux the solvent and separate the water of reaction:

(i) 47 g of phenol (0.5 mole);

(ii) 31 g of boric acid (0.5 mole);

(iii) 15 g of toluene.

The mixture was distilled for 3 hours and the carrier (toluene) was recycled to separate the theoretical amount of water.

Dilution with 75 g of toluene was next carried out and 16 g of trioxymethylene suspended in 25 g of toluene were added. The mixture was maintained at 80° C. until the reaction with the formaldehyde was complete (about 3 hours).

The solution of saligenine borate in toluene was hydrolyzed at room temperature with a caustic soda solution prepared by adding 200 g of water to 152 g of a 30% by weight caustic soda aqueous solution. This was then decanted and the aqueous solution containing the sodium salts of saligenol and boric acid was separated out.

This aqueous solution was oxidized directly using the procedure described in Example 4, except that it was not necessary to add boric acid.

Oxygen, at atmospheric pressure, was introduced into the solution, to which the following had been added:

(a) 0.8 g of 2% platinum black (16 mg of platinum), (b) 0.035 g of bismuth oxide (31 mg of bismuth), until the volume of oxygen absorbed corresponded to the theoretical amount required to transform the saligenol into salicylic aldehyde, namely, about 1 hour.

The catalyst was separated from the reaction mixture and the salicylic aldehyde formed was liberated from its sodium salt by adding 200 ml of 5N sulfuric acid, then steam distilling or extracting using an appropriate solvent to isolate the salicylic aldehyde.

43 g of salicylic aldehyde were obtained, representing a yield of 68% with respect to the beginning phenol.

EXAMPLE 6

The procedure of Example 5 was repeated, but without the addition of bismuth oxide to the aqueous solution containing the sodium salts of saligenol and boric acid (before oxidation).

23 g of salicylic aldehyde were obtained, i.e., a yield of 37% with respect to the beginning phenol.

EXAMPLE 7

The following reagents were introduced into a three necked flask provided with a thermometer, a distillation column, a retrograder, a coolant and a separator:

(i) salicylic aldehyde (600 mmol) prepared in accordance with Example 5;

(ii) acetic anhydride (1.90 mmol) in solution in acetic acid (3.47 g).

The mixture was refluxed and sodium acetate (2.1 mmol) was introduced in solution in acetic acid (3.47 g).

The acetic acid was distilled by maintaining the reflux until the temperature at the column head was about 118° C.

After 2 hours, 50 minutes, of reaction, gas chromatographic determination of the cumarin evidenced a yield of 82% thereof.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of a hydroxybenzaldehyde, comprising oxidizing the corresponding hydroxybenzyl alcohol with oxygen, in liquid phase, in an aqueous reaction medium which comprises an alkali, in the presence of (i) a catalytically effective amount of a platinum compound and (ii) a cocatalytically effective amount of both boron and bismuth compounds.

2. The process as defined by claim 1, said hydroxybenzyl alcohol having the formula (I):

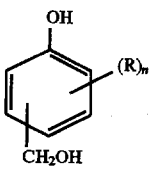

in which the radical —$CH_2OH$ is in the ortho-, meta- or para-position to the hydroxy group, R is one or more inert substituents, which may be identical or different, and n is a number less than or equal to 3.

3. The process as defined by claim 2, wherein formula (I), each R is a hydrogen atom, a halogen atom, or an alkyl or alkoxy radical having from 1 to 12 carbon atoms.

4. The process as defined by claim 3, wherein formula (I), each R is hydrogen, fluorine, chlorine, bromine, or an alkyl or alkoxy radical having from 1 to 4 carbon atoms.

5. The process as defined by claim 1, wherein said hydroxybenzyl alcohol is saligenol.

6. The process as defined by claim 1, comprising oxidizing said hydroxybenzyl alcohol with molecular oxygen or an oxygen-containing gas.

7. The process as defined by claim 1 wherein said boron compound is selected from a boric acid, a metal borate, or a boron double salt.

8. The process as defined by claim 7, wherein said boron compound is selected from orthoboric acid or $B_2O_3$ precursor thereof, metaboric acid, pyroboric acid, tetraboric acid, an alkali or alkaline earth metal or ammonium borate, or a metal fluoborate.

9. The process as defined by claim 8, wherein said boron compound is selected from a metal or ammonium tertiary borate, hemiborate, monoborate, diborate, triborate, tetraborate or pentaborate.

10. The process as defined by claim 8, wherein said boron compound is orthoboric acid or boric anhydride.

11. The process as defined by claim 7, wherein the ratio between the number of moles of boron compound and the number of moles of starting hydroxybenzyl alcohol ranges from 0.1 to 3.0.

12. The process as defined by claim 11, said ratio ranging from 0.9 to 1.1.

13. The process as defined by claim 1, wherein said bismuth compound is selected from a bismuth oxide, a bismuth hydroxide, a bismuth or bismuthyl salt of an inorganic hydracid, a bismuth or bismuthyl salt of an inorganic oxyacid, a bismuth or bismuthyl salt of aliphatic or aromatic carboxylic acid, or a bismuth or bismuthyl phenate.

14. The process as defined by claim 13, wherein said bismuth compound is selected from a bismuth or bismuthyl chloride, bromide, iodide, sulfide, selenide, telluride, sulfite, sulfate, nitrite, nitrate, phosphite, phosphate, pyrophosphate, carbonate, perchlorate, antimonate, arsenate, selenite, selenate, acetate, propionate, salicylate, benzoate, oxalate, tartrate, lactate, citrate, gallate or pyrogallate.

15. The process as defined by claim 13, wherein said bismuth compound is selected from $Bi_2O_3$, $Bi_2O_4$, $Bi(OH)_3$, $BiCl_3$, $BiBr_3$, $BiI_3$, $Bi_2(SO_4)_3$, $Bi(NO_3)_3 \cdot 5H_2O$, $(BiO)NO_3$, $(BiO)_2CO_3 \cdot 5H_2O$, $Bi(C_2H_3O_2)_3$ or $C_6H_4CO_2(BiO)(OH)$.

16. The process as defined by claim 13, said medium of reaction comprising at least 0.1% by weight of metallic bismuth relative to the weight of platinum and 10 to 900 ppm by weight of metallic bismuth relative to the hydroxybenzyl alcohol.

17. The process as defined by claim 1, wherein said platinum compound is selected from platinum black, platinum oxide, or platinum metal deposited onto support therefor.

18. The process as defined by claim 17, wherein said platinum compound is selected from platinum metal deposited onto carbon black, calcium carbonate, alumina or silica.

19. The process as defined by claim 1, wherein the amount of platinum compound employed, expressed by weight of metallic platinum relative to the hydroxybenzyl alcohol, ranges from 0.01% to 4%.

20. The process as defined by claim 19, said amount ranging from 0.04% to 2%.

21. The process as defined by claim 1, said medium of reaction comprising 0.5 to 3 moles of sodium or potassium hydroxide relative to the hydroxybenzyl alcohol.

22. The process as defined by claim 1, carried out at a temperature ranging from 10° C. to 100° C.

23. The process as defined by claim 22, carried out at a temperature ranging from 20° C. to 60° C.

24. The process as defined by claim 1, wherein said hydroxybenzyl alcohol is a complex salt of hydroxybenzyl alcohol and said boron compound is boric acid.

25. The process as defined by claim 24, wherein said complex salt of hydroxybenzyl alcohol and boric acid is formed by reacting a phenol with boric acid or boric anhydride and forming a boric ester, reacting said boric ester with formaldehyde or a formaldehyde generator and forming a hydroxybenzyl alcohol borate, and ten saponifying said hydroxybenzyl alcohol borate into said complex salt of hydroxybenzyl alcohol and boric acid.

26. The process as defined by claim 25, wherein said hydroxybenzyl alcohol is saligenol.

27. The process as defined by claim 25, wherein the molar ratio phenol/boric acid ranges from 0.8 to 3.0.

28. The process as defined by claim 27, said molar ratio ranging from 1.0 to 1.5.

29. The process as defined by claim 1, comprising preparing salicylaldehyde.

* * * * *